(12) United States Patent
Mäntylä

(10) Patent No.: US 9,745,697 B2
(45) Date of Patent: Aug. 29, 2017

(54) MEASUREMENT OF WEB

(71) Applicant: VALMET AUTOMATION OY, Espoo (FI)

(72) Inventor: Markku Mäntylä, Kangasala (FI)

(73) Assignee: VALMET AUTOMATION OY, Espoo (FI)

( * ) Notice: Subject to any disclaimer, the term of this patent is extended or adjusted under 35 U.S.C. 154(b) by 35 days.

(21) Appl. No.: 14/894,463

(22) PCT Filed: May 28, 2014

(86) PCT No.: PCT/FI2014/050424
§ 371 (c)(1),
(2) Date: Nov. 27, 2015

(87) PCT Pub. No.: WO2014/191626
PCT Pub. Date: Dec. 4, 2014

(65) Prior Publication Data
US 2016/0122946 A1  May 5, 2016

(30) Foreign Application Priority Data

May 29, 2013 (FI) ..................................... 20135590

(51) Int. Cl.
*D21F 7/00* (2006.01)
*B65H 7/02* (2006.01)
(Continued)

(52) U.S. Cl.
CPC .......... *D21F 7/003* (2013.01); *B05C 11/1015* (2013.01); *B65H 7/02* (2013.01);
(Continued)

(58) Field of Classification Search
CPC .... D21G 9/0009; D21G 9/0036; G01N 21/86; G01N 2021/8609; G01N 2021/8645;
(Continued)

(56) References Cited

U.S. PATENT DOCUMENTS 4,437,917 A * 3/1984 Tao ........................... D21F 7/06
156/296
4,484,133 A * 11/1984 Riggin ................... G01N 22/04
324/606
(Continued)

FOREIGN PATENT DOCUMENTS

DE  10 2011 083 653 A1  3/2013
EP   1 273 879 A2  1/2003
(Continued)

OTHER PUBLICATIONS

Mar. 13, 2014 Search Report issued in Finnish Patent Application No. 20135590.
(Continued)

*Primary Examiner* — Lisa Caputo
*Assistant Examiner* — Philip Cotey
(74) *Attorney, Agent, or Firm* — Oliff PLC

(57) ABSTRACT

An apparatus including a caliper measuring sensor arrangement, a mass measuring sensor arrangement, and a stabilizing arrangement. The caliper measuring sensor arrangement measures caliper of the web. The mass measuring sensor arrangement measures at least one of the following: a basis weight of the web, a moisture content, a water weight, dry weight of the web. The stabilizing arrangement stabilizes the web. The stabilizing arrangement including at least a part of the mass measuring sensor arrangement.

13 Claims, 4 Drawing Sheets

(51) Int. Cl.
| | |
|---|---|
| *D21F 7/06* | (2006.01) |
| *G01B 7/06* | (2006.01) |
| *G01B 11/06* | (2006.01) |
| *D21G 9/00* | (2006.01) |
| *B05C 11/10* | (2006.01) |
| *G01G 17/02* | (2006.01) |
| *G01N 21/86* | (2006.01) |
| *G01N 33/34* | (2006.01) |

(52) U.S. Cl.
CPC ............ *D21F 7/06* (2013.01); *D21G 9/0009* (2013.01); *G01B 7/06* (2013.01); *G01B 11/06* (2013.01); *G01B 11/0691* (2013.01); *G01G 17/02* (2013.01); *G01N 21/86* (2013.01); *G01N 33/34* (2013.01)

(58) Field of Classification Search
CPC ... G01N 2021/8654; G01N 2021/8663; G01N 2021/8672; G01N 33/346; G01N 33/34; G01N 33/343; D21F 7/003; D21F 7/06; G01B 11/06; G01B 11/0691; B61H 2511/13; D04H 1/425; D21H 23/12; B05C 11/1015; B65H 7/02; G01G 17/02
See application file for complete search history.

(56) References Cited

U.S. PATENT DOCUMENTS

| | | | | |
|---|---|---|---|---|
| 4,789,820 A * | 12/1988 | Parrent, Jr. | ............ | G01N 22/04 324/640 |
| 5,094,535 A | 3/1992 | Dahlquist et al. | | |
| 5,349,845 A * | 9/1994 | Blom | ........................ | D21F 1/32 162/263 |
| 5,745,244 A * | 4/1998 | Svanqvist | ............ | D21G 9/0009 162/263 |
| 6,188,077 B1 * | 2/2001 | Lind | ..................... | G01N 33/346 118/419 |
| 6,281,679 B1 * | 8/2001 | King | ..................... | G01B 7/107 324/226 |
| 7,423,435 B2 | 9/2008 | Sawamoto et al. | | |
| 2001/0028459 A1 * | 10/2001 | Hartenstein | ............ | B65H 26/00 356/429 |
| 2002/0104635 A1 * | 8/2002 | Wells | ................... | G01N 33/346 162/198 |
| 2002/0134523 A1 * | 9/2002 | Mantyla | ................... | D21F 5/042 162/263 |
| 2002/0144546 A1 * | 10/2002 | Moisio | ................... | G01B 21/06 73/159 |
| 2003/0024301 A1 * | 2/2003 | Graeffe | ............. | G01B 11/0691 73/37.6 |
| 2003/0117492 A1 * | 6/2003 | Jokela | .................... | B65H 26/02 348/88 |
| 2003/0150266 A1 * | 8/2003 | Dammig | .............. | D01G 31/006 73/433 |
| 2003/0216828 A1 * | 11/2003 | Puurtinen | ............ | D21G 9/0027 700/128 |
| 2003/0222219 A1 * | 12/2003 | Almi | ...................... | D21F 7/003 250/341.2 |
| 2004/0060352 A1 * | 4/2004 | Cherif | ..................... | D01H 5/38 73/159 |
| 2004/0069059 A1 * | 4/2004 | Shakespeare | ........ | D21G 9/0009 73/159 |
| 2004/0128856 A1 * | 7/2004 | Bjornberg | .............. | D21F 5/002 34/443 |
| 2005/0021262 A1 * | 1/2005 | Mantyla | ............... | D21G 9/0009 702/76 |
| 2005/0103095 A1 * | 5/2005 | Ulfert | .................. | D21G 9/0036 73/38 |
| 2005/0157314 A1 | 7/2005 | Typpoe et al. | | |
| 2006/0288782 A1 * | 12/2006 | Sawamoto | ........... | D21G 9/0009 73/579 |
| 2007/0145307 A1 | 6/2007 | Duck et al. | | |
| 2008/0136091 A1 | 6/2008 | Shakespeare | | |
| 2009/0029619 A1 * | 1/2009 | Kovalainen | ............ | D04H 1/425 442/334 |
| 2009/0056412 A1 * | 3/2009 | Graeffe | ................. | D21G 9/0009 73/1.81 |
| 2009/0101297 A1 * | 4/2009 | Jez | ......................... | G01N 21/23 162/198 |
| 2009/0126888 A1 * | 5/2009 | Banks | ...................... | D21C 7/12 162/158 |
| 2009/0134565 A1 | 5/2009 | Duan | | |
| 2009/0260771 A1 | 10/2009 | Alev et al. | | |
| 2010/0043993 A1 * | 2/2010 | Pihola | .................. | D21G 9/0045 162/198 |
| 2011/0108224 A1 * | 5/2011 | Yazaki | .................. | D21F 7/083 162/100 |
| 2013/0220158 A1 * | 8/2013 | Vassilev | ............ | G01N 21/3559 101/484 |

FOREIGN PATENT DOCUMENTS

| | | |
|---|---|---|
| EP | 1 734 361 A1 | 12/2006 |
| WO | 2011/138509 A1 | 11/2011 |

OTHER PUBLICATIONS

Sep. 9, 2014 Search Report issued in International Patent Application No. PCT/FI2014/050424.

Sep. 9, 2014 Written Opinion issued in International Patent Application No. PCT/FI2014/050424.

* cited by examiner

MEASUREMENT OF WEB

FIELD

The invention relates to a measurement of web.

BACKGROUND

Physical properties of a web of paper can be measured with different sensors. However, there are problems related to the measurements. The measurements devices require too much space, and the accuracy and reliability of the measurements are not as good as desired.

Hence, there is a need to develop the measurements.

BRIEF DESCRIPTION

The object of the invention is to provide an improved solution. This is achieved by a measuring device of claim 1.

The invention also relates to a process system of producing web in accordance with claim 11.

The invention also relates to a controlling system in accordance with claim 12.

The invention further relates to a measuring method in accordance with claim 14.

Preferred embodiments of the invention are disclosed in the dependent claims.

The invention provides advantages. The web is stabile during a measurement which becomes accurate and reliable. The sensor arrangement near the web may also be compact.

LIST OF FIGURES

The invention will now be described in greater detail in connection with preferred embodiments, with reference to the accompanying drawings, in which.

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide further embodiments. Moreover, words "comprising" and "including" should be understood as not limiting the described embodiments to consist of only those features that have been mentioned but such embodiments may contain also features/structures that have not been specifically mentioned.

It should be noted that while Figures illustrate various embodiments, they are simplified representations that only show some structures and/or functional entities. It is apparent to a person skilled in the art that the described apparatuses may also comprise other functions and structures. It should be appreciated that some features of functions, structures, and the protocols used for interaction may be irrelevant to the actual invention. Therefore, such features need not be discussed in more detail here. Although separate single entities have been depicted, different parts may be implemented in one or more physical or logical entities.

Figure 1:
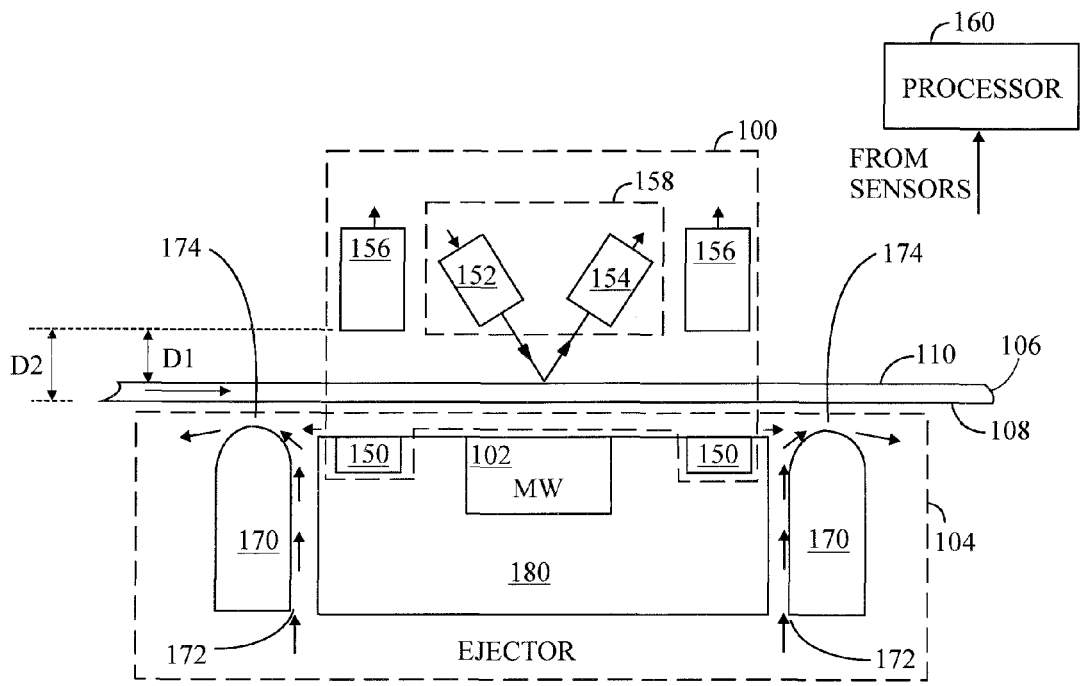
FIG. 1 illustrates an example of a measuring head having a stabilizer and sensors for measuring at least two properties of a web.

FIG. 1 presents a sensor structure of an apparatus for measuring a moving web 106. The movement of the web 106 is presented with an arrow in FIG. 1. The movement of the web 106 may also be the opposite shown in FIG. 1. The web 106 may be for example a paper web, board web, tissue web, pulp web or any other similar fiber web. The web 106 may also be a sheet made of fibers. The sensor structure comprises a caliper measuring sensor arrangement 100, a mass measuring sensor arrangement 102, and a stabilizing arrangement 104 which includes at least a part of the mass measuring sensor arrangement 102. The stabilizing arrangement 104 stabilizes the web 106. The stabilizing arrangement 104 may set a first surface 108 of the web 106 and the stabilizing arrangement 104 in a stabilized position with each other. As a result, the apparatus may perform the measurements in a semi-contacting manner. The moving web 106 may actually be in a physical contact with the stabilizing arrangement 104 or there may be a gap between the stabilizing arrangement 104 and the web 106. The potential gap is a controlled gap providing stabilization of the web 106 in a perpendicular direction with respect to the actual movement of the web 106 in the machine direction. A surface of the stabilizing arrangement 104 may be a plate-like structure which is on one side of the web 106 and by which the web 106 is supported during the movement. The surface of the stabilizing arrangement 104 may be made of metal, ceramic or plastic, for example.

The caliper measuring sensor arrangement 100 measures the caliper of the stabilized web 106. The mass measuring sensor arrangement 102 measures at least one of the following from the web: a basis weight, a water weight, a moisture content, a dry weight. Also the mass measurement measures the stabilized web 106. A moisture content of the web 106, which may be expressed in percentage, can be formed on the basis of the basis weight and the water weight in the sensor arrangement 102 or in the processor 160. The unit of the basis weight and/or may be $kg/m^2$, $kg/m^3$ or their derivatives, for example. The moisture content may be measured using absolute units or relative units. The unit of the water weight may be $kg/m^2$, $kg/m^3$ or their derivatives, for example. The moisture content in percentages may be formed by dividing the water weight by the basis weight and multiplying the result by 100%. The dry weight, in turn, may be formed by subtracting the water weight from the basis weight.

Figure 2:
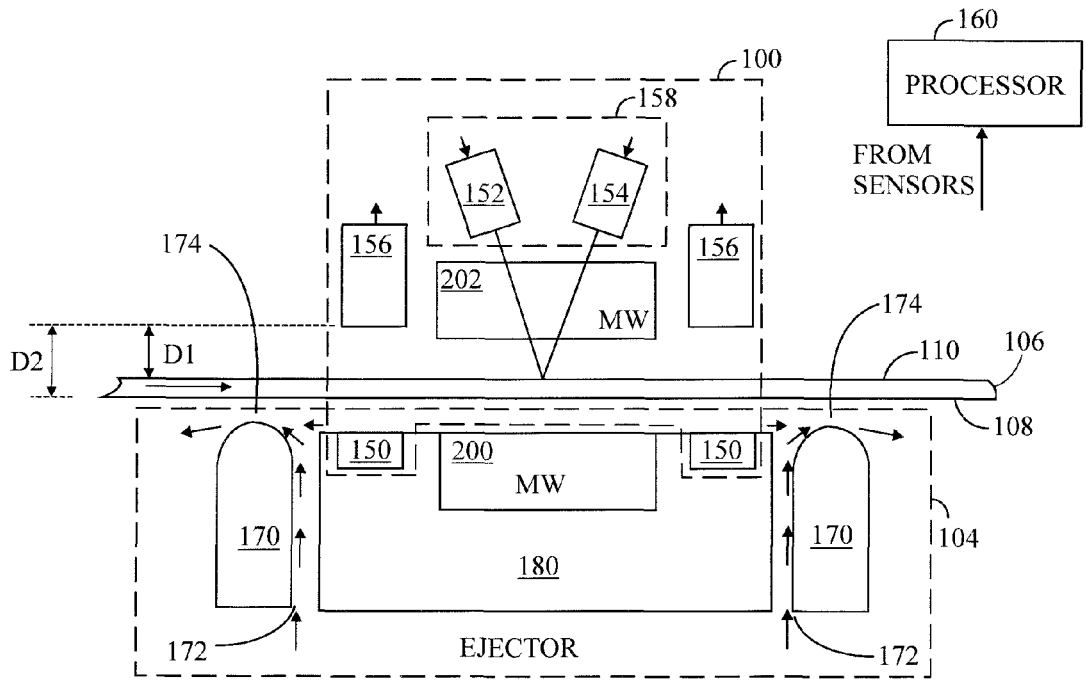
FIG. 2 shows another example of a measuring head having a stabilizer and sensors for measuring at least two properties of a web.

As shown in FIGS. 1 and 2, the stabilizing arrangement 104 includes at least a part of the mass measuring sensor arrangement 102. The stabilizing arrangement 104 may also include at least one element 150 of the caliper measuring sensor arrangement 100. The caliper measuring sensor arrangement 100 may further comprise a plurality of caliper sensor elements 152, 154 on an opposite surface 110 of the web 106 with respect to the first surface 108. According to the example of FIG. 1, the mass measuring sensor arrangement 102 is in the stabilizing arrangement 104. According to the example of FIG. 2, the mass measuring sensor arrangement 102 is partly in the stabilizing arrangement 104.

In an embodiment, the stabilizing arrangement 104 may comprise an ejector configured to exert negative pressure on the web 106 by withdrawing gas from between a surface of the stabilizing arrangement 104 and the first surface 108 of the web 106. Thus, the stabilizing arrangement 104 may provide a vacuum between the stabilizing arrangement 104 and the web 106 for stabilizing the web 106.

Figure 3:
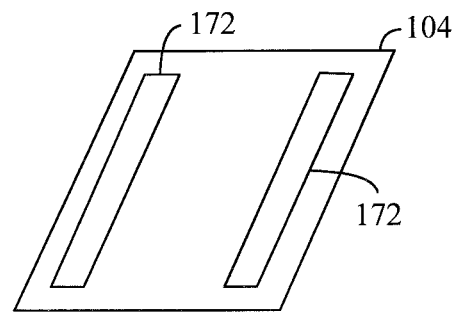
FIGS. 3 to 5 show examples of cross section of nozzle gaps.
Figure 4:
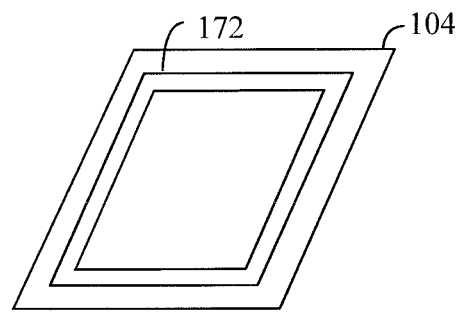
Figure 5:
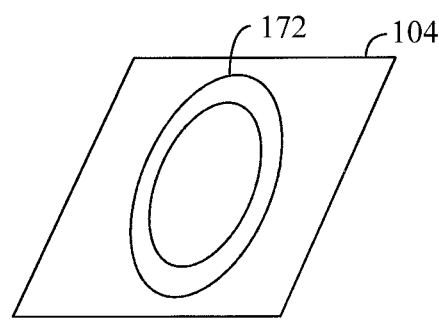

The ejector of stabilizing arrangement 104 may comprise a nozzle gap 172, a discharge gap 174 and a guide structure 170. The nozzle gap 172 is between main body 180 of the stabilizing arrangement 104 and the guide structure 170. The guide structure 170 may be made of metal, ceramic or plastic, for example. A cross section of the guide structure 170 may be round like a circle or an ellipse or the shape of the cross section may be a square or a rectangle. However, the guide structure 170 may also comprise two separate parts which may be perpendicular to the direction of movement of the web 106. The shapes of cross sections of the nozzle gap 172 are shown in FIGS. 3, 4 and 5. The nozzle gap 172 may receive a gas flow from an external pressure container or gas pump, which gas flow may discharge from the discharge gap 174 for generating low pressure between the web 106 and the stabilizing arrangement 104. The low pressure draws the web 106 towards the stabilizing arrangement 104 reducing a degree of freedom of movement of the web 106. The measurement performed by an ejector has an advantage that filtering of dirt, dust and moisture is not necessarily needed.

In an embodiment, the stabilizing arrangement 104 may suck the first surface 108 of the web 106 and the stabilizing arrangement 104 in contact with each other for stabilizing vibration of the web 106 in a direction crosswise with respect to the movement of the web 106.

In an embodiment, the vacuum may be generated by a vacuum generator.

In an embodiment, the caliper measuring sensor arrangement 100 may comprise at least one optical sensor 158 configured to provide information about a distance between the optical sensor 158 and the opposite surface 110 of the web 106 with respect to the first surface 108. The caliper measuring sensor arrangement 100 may also comprise at least one electromagnetic sensor element 156 configured to provide information about the distance between the optical sensor 158 and the stabilizing arrangement 104 for determination of the caliper of the web 106. The caliper of the web 106 can be considered to express a property the same as or similar to a thickness of the web 106. The at least one electromagnetic sensor element 156 may provide the information about the distance between the optical sensor 158 and the stabilizing arrangement 104 in association with the at least one element 150 of the caliper measuring sensor arrangement 100 included in the stabilizing arrangement 104.

Let us now examine the caliper measurement in more detail. The caliper of the web 106 may also be called caliper. To measure caliper of the web 106 the positions of its first surface 110 and second surface 108 should be determined. The optical measuring sensor 158 may comprise a transmitter part 152 for transmitting optical radiation towards the web 106. The transmitter part 152 may comprise at least one laser or led, for example. The optical measuring sensor 158 may comprise a receiver part 154 for receiving a part of the transmitted optical radiation as a reflection from the second surface 110 of the web 110. The receiver part 154 may comprise at least one semiconductor photodetector such as a photodiode. The reflection here means a specular reflection and/or a diffuse reflection. The optical band of the transmitter part 152 is within a range 106 about 100 nm to 1 mm. More typically the band of the transmitter part 152 is within at least one of the following: infrared light, visible light, ultraviolet light. The optical measuring sensor 158 and a processor 160 may be used to measure or determine a distance D1 between the optical measuring sensor 158 and the moving web 106, i.e. the second surface 110 of the moving web 106. The optical measuring sensor 158 and the processor 160 may measure the distance D1 using triangulation method. The optical measuring sensor 158 and the processor 160 may utilize a confocal chromatic aberration method, for instance.

The electromagnetic measuring sensor elements 150, 156 and the processor 160 may measure or determine a distance D2 between the optical measuring sensor 158 and the stabilizing arrangement 104. The distance D2 is related to the distance between the optical measuring sensor 158 and the first surface 108 of the web 106. Two electromagnetic measuring sensor elements 150, 156 form a pair one of which faces the first surface 108 of the web 106 and another of which is on the second surface 110 of the web 106. Of a pair, one electromagnetic measuring sensor element 150 (156) may be coil and another electromagnetic measuring sensor element 156 (150) may be made of a material that conducts electricity well, such as steel, aluminium, copper or the like. This may be the same material as that of the stabilizing arrangement 104. That is why it is possible, in an embodiment, that the sensor element 150 is not a materially separate part of the stabilizing arrangement 104. The distance between the electromagnetic measuring sensor elements 150, 156 may be determined in an inductive manner known per se to a person skilled in the art. The distance between the electromagnetic measuring sensor elements 150, 156 may directly represent the distance D2 between the optical measuring sensor 158 and the stabilizing arrangement 104 or it may be used to determine that in a predetermined manner because the web 106 is stabilized. This distance may also be determined capacitively or in some other electromagnetic way suitable for a measurement made through the web 106. The caliper t of the web 106 is or is related to difference between distances D2 and D1, $t=f(D2-D1)$, where f is a suitable function. The function f may correspond at least approximately to multiplication with number one.

In an embodiment, the mass measuring sensor arrangement 102 may comprise at least one microwave resonator sensor or at least one microwave transceiver sensor. In an embodiment, the at least one microwave resonator sensor may comprise at least one dielectric resonator.

In an embodiment, the microwave resonator sensor of the mass measuring sensor arrangement 102 and the processor 160 may measure basis weight of the web 106 on the basis of resonance frequency shift caused by the web 106. The basis weight may also be called grammage.

In an embodiment, the microwave resonator sensor of the mass measuring sensor arrangement 102 and the processor 160 may measure water weight of the web 106 on the basis of a peak or height level of the resonance frequency, where the peak level depends on water weight of the web 106.

In an embodiment, the microwave resonator sensor of the mass measuring sensor arrangement 102 and the processor 160 may measure water weight of the web 106 on the basis of a Q value of the resonance frequency, where the Q value depends on water weight of the web 106. The measurements of basis weight and water weight per se are described in more detail in patent publication EP 1734361.

In an embodiment, the mass measuring sensor arrangement 102 as a whole may be a part of the stabilizing arrangement 104. That means that the mass measuring sensor arrangement 102 may be inside the stabilizing arrangement 104. Alternatively, the mass measuring sensor arrangement 102 may have a place in the stabilizing arrangement 104 such that the mass measuring sensor arrangement 102 is fully or partly within the stabilizing arrangement 104. The mass measuring sensor arrangement 102 may be attached or integrated to the stabilizing arrangement 104.

In an embodiment shown in FIG. 2, the mass measuring sensor arrangement 102 may have at least two parts 200, 202. The moving web 106 may be located between the first part 200 and the second part 202 of the mass measuring sensor arrangement 102. The first part 200 of the mass measuring sensor arrangement 102 may be located in the stabilizing arrangement 104 over the first side 108 of the web 106. The second part 202 of the mass measuring sensor arrangement 102 may be located on the opposite side 110 of the web 106. The second part 200 of the mass measuring sensor arrangement 102 may be at least partly transparent to the optical radiation transmitted by the transmitter part 152 for enabling the caliper measurement. The material of the second part 200 of the mass measuring sensor arrangement 102 may itself be transparent i.e. have low attenuation of the optical radiation or the material may have at least one optical hole for allowing the optical radiation to pass therethrough. The transmitter part 152 and the receiver part 154 may be at least partly inside the second part 200 of the mass measuring sensor arrangement 102. However, it is possible that the transmitter part 152 and the receiver part 154 are outside the second part 202 of the mass measuring sensor arrangement 102.

In an embodiment, the mass measuring sensor arrangement 102 may comprise at least one capacity sensor responsive to capacity of the web 106. The capacity sensor has two electrically conductive terminals which are separated from each other. When the web 106 is closely beside or between the conductive terminals, the capacitance of the sensor depends on the basis weight and/or water weight of the web 106. In an embodiment, the capacity may be measured from the first surface 108 by having both terminals on the first surface 108. In an embodiment, the capacity may be measured from the second surface 110 by having both terminals on the second surface 110. In an embodiment, the capacity may be measured from through the web 106 by having the terminals on different sides of the web 106. The capacitance measurement is known per se by a person skilled in the art.

The first part 200 and the second part 202 may comprise parts of a microwave resonator the resonance frequency of which is a function of a basis weight and/or water weight of the web 106 placed between the first part 200 and the second part 202. Additionally or alternatively, the first part 200 and the second part 202 may comprise terminals of a capacity sensor.

In an embodiment, at least one sensor of the mass measuring sensor arrangement 102 may be in physical contact with web 106.

In an embodiment, the mass measuring sensor arrangement 102 and the caliper measuring sensor arrangement 100 may measure the web 106 at locations at least partly common to the caliper and mass measurements. When caliper and at least one of the moisture content and basis weigh are measured at the same location simultaneously, they give precise and directly comparable information about the state of the web 106. This improves the controllability of the manufacturing process of an end product such as paper, for example. Also quality of the end product becomes better.

In an embodiment, a processing unit 160 determines density of the web 106 on the basis of the measurements of the web 106 made by the caliper measuring sensor arrangement 100 and the mass measuring sensor arrangement 102.

In an embodiment, a process system which comprises the above described measurement system and which produces the web 106 may also comprise at least one of the following: a paper machine, a pulp drier, a coating machine.

In an embodiment, a controlling system may control the process producing the web 106. Then the controlling system may comprise a controller controlling at least one actuator of the process system on the basis of the measurements made by the caliper measuring sensor arrangement 100 and the mass measuring sensor arrangement 104 in accordance with any of the various embodiments described in this application.

In an embodiment, a controlling system may comprise one or more processors, one or more memories and a suitable computer program code stored in the one or more memories. The one or more memories and the computer program code may, with the one or more processors, cause the controlling system at least to perform at least one measurement of caliper and at least one measurement of mass of the web 106. The measurement of mass may be a measurement of at least one of the following: a basis weight, a water weight, a dry weight, a moisture content. The one or more memories and the computer program code may then, with the one or more processors, cause the controlling system at least to control the at least one actuator of the process system on the basis of the measurements.

Figure 6:
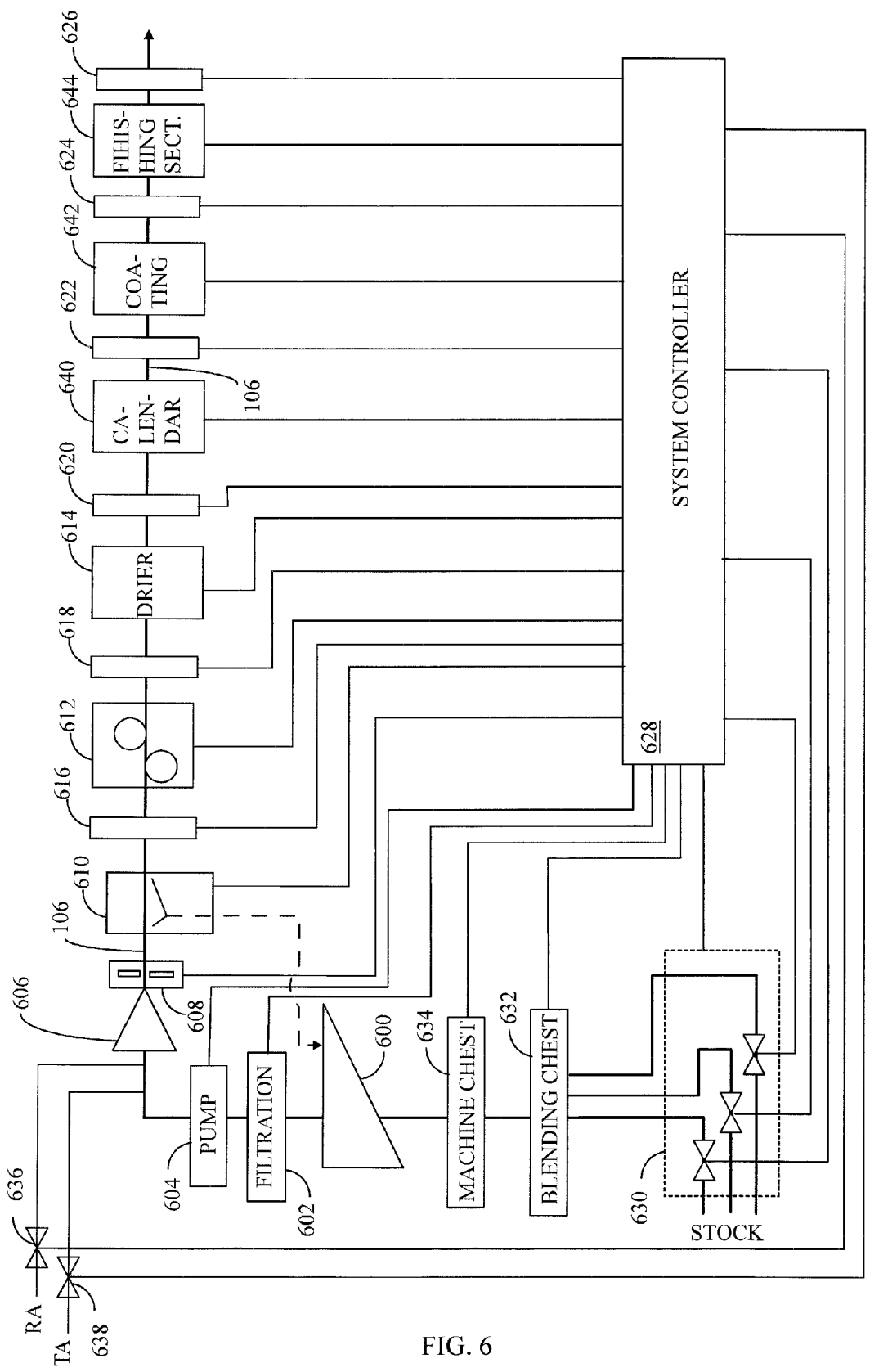
FIG. 6 shows an example of a paper machine.

FIG. 6 shows an exemplary of the structure of a paper machine in principle. One or more stocks are fed onto a paper machine through a wire pit silo 600, which is usually preceded by a blending chest 632 for partial stocks and a machine chest 634. The machine stock is dispensed for a short circulation, for instance, controlled by a basis weight control or a grade change program. The blending chest 632 and the machine chest 634 may also be replaced by a separate mixing reactor (not shown in FIG. 6), and the dispensing of the machine stock is controlled by feeding each partial stock separately by means of valves or another flow control means 630. In the wire pit silo 600, water is mixed into the machine stock to obtain a desired consistency for the short circulation (dashed line from a former 610 to the wire pit silo 600). From the obtained stock it is possible to remove sand (centrifugal cleaners), air (deculator) and other coarse material (pressure filter) using cleaning devices 602, and the stock is pumped with a pump 604 to a headbox 606. Before the headbox 606, it is possible to add to the stock, in a desired manner, a filler TA, including e.g. gypsum, kaolin, calcium carbonate, talcum, chalk, titanium dioxide and diatomite etc. and/or a retention agent RA, such as inorganic, inartificial organic or synthetic water-soluble organic polymers through valves 636, 638. With fillers it is possible to reduce the porosity in the paper web, for instance, because fine-grained filler tends to fill air channels and cavities. This is observed in formation and surface properties, opacity, brightness and printability. The retention agents RA, in turn, increase the retention of the fines and fillers while speeding up dewatering in a manner known per se. Both the fillers and the retention agents thus affect the structural properties of the paper, such as porosity, which can be seen in optical properties and smoothness of surface as well as topography.

From the headbox 606 the stock is fed through a slice opening 608 of the headbox to a former 610, which may be a fourdrinier wire or a gap former. In the former 610, water drains out of the web 106 and additionally ash, fines and fibres are led to the short circulation. In the former 610, the stock is fed onto a wire, and the forming web 106 is preliminarily dried and pressed in a press 612, which affects porosity. The web 106 is actually dried in driers 614. Conventionally, the paper machine comprises at least one measuring device component 620, 622, 624, 626, which comprises measuring sensors 102, 150, 156, 158 and the stabilizing arrangement 104. In the cross direction of the web 106 there may be a row of several measuring device components for measuring a cross-directional profile of a property of the web 106. Alternatively, one or more measuring devices may be scanning back and forth over the width of the web 106. With the measuring device components 616 and 618 also refer to other sensors with which it is possible to perform other measurements known per se. A system controller 628 may receive signals from the measuring device components 620 to 626, and control various actuators on the basis of the measurements relating to caliper, moisture and/or basis weight, for example. The system controller 628 may comprise the processor 160.

The paper machine, which in connection with this application refers to paper or board machines, may also include a pre-calendar 640, a coating section 642 and/or a finishing calendar 644, the operation of which affects the porosity. It is not necessary to have the coating section 642, however, and therefore it is not necessary to have more calendars 640, 644 than one. In the coating section 642, coating paste, which may contain e.g. gypsum, kaolin, talcum or carbonate, starch and/or latex, may be spread onto paper.

In calendars 640, 644, where the uncoated or coated paper or board web runs between the rolls pressing with desired force, it is possible to change the properties of the paper. In the calendars 640, 644, the properties of the paper web may be changed by means of web moistening, temperature and nip pressure between the rolls such that the higher the pressure exerted on the web, the smoother and glossier the paper will be. In addition to this, it is clear that the operation of a paper machine is known per se to a person skilled in the art, and therefore, it need not be presented in greater detail in this context.

The system controller 628, which may perform signal processing, may control various process of the paper machine on the basis of the measurements such that properties of the paper to be manufactured, will meet the set requirements. The system controller 628 may also present the measured properties graphically and/or numerically on a desired scale and according to a desired standard on a display, for instance.

The system controller 628 may be conceived as a paper machine's control arrangement, or part thereof, based on automatic data processing. The system controller 628 may receive digital signals or analog signals which may be converted to digital ones. The system controller 628 may comprise a processor and memory and execute the signal processing and the paper machine control in accordance with appropriate computer programs. The operating principle of the system controller 628 may be, for instance, PID (Proportional-Integral-Derivative), MPC (Model Predictive Control) or GPC (General Predictive Control) control.

Figure 7:
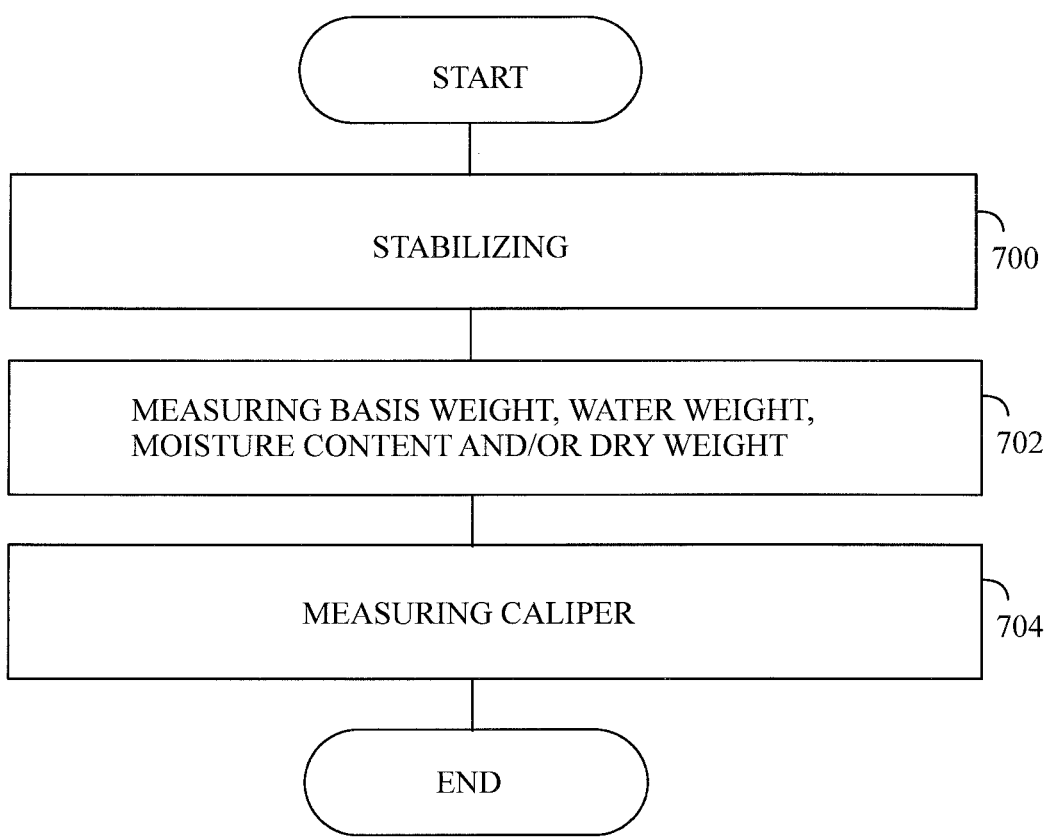
FIG. 7 is a flow chart of a method.

FIG. 7 is a flow chart of the measuring method. In step 700, the moving web is stabilized by a stabilizing arrangement, which includes at least a part of the mass measuring sensor arrangement. In step 702, at least one of the following is measured by a mass measuring sensor arrangement from the moving web: a basis weight of the web, a water weight, a moisture content, dry weight. In step 704, caliper of the moving web measuring is measured by a caliper measuring sensor arrangement. The stabilization enables the caliper and mass measurements. With the stabilization of the web 106, the measurements are accurate resulting in good control of the manufacturing process and excellent quality of the end product of the process.

Even though the invention is described above with reference to the examples of the attached drawings, it is clear that the invention is not restricted thereto, but it may be modified in a variety of ways within the scope of the accompanying claims.

The invention claimed is:

1. An apparatus for measuring a moving web, wherein the apparatus comprises a caliper measuring sensor arrangement, a mass measuring sensor arrangement, and a stabilizing arrangement;
the stabilizing arrangement is configured to stabilize the web and comprising in an integrated manner at least a part of the mass measuring sensor arrangement and at least a part of the caliper measuring sensor arrangement, and the stabilizing arrangement being configured to withdraw gas from between the first surface of the web and a surface of the stabilizing arrangement;
the caliper measuring sensor arrangement is configured to measure caliper of the web optically; and
the mass measuring sensor arrangement comprises at least one microwave resonator sensor or at least one microwave transceiver sensor for measuring weight of the web on the basis of at least one the following: a basis weight of the web, a water weight of the web, a moisture content of the web, and a dry weight.

2. The apparatus of claim 1, wherein the mass measuring sensor arrangement as a whole is a part of the stabilizing arrangement.

3. The apparatus of claim 1, wherein a first part of the mass measuring sensor arrangement is located in the stabilizing arrangement on the first side of the web and a second part of the mass measuring sensor arrangement is located on the opposite side of the web.

4. The apparatus of claim 2, wherein the at least one microwave resonator sensor comprises at least one dielectric resonator.

5. The apparatus of claim 2, wherein the mass measuring sensor arrangement comprises at least one electric capacitance sensor responsive to electric capacitance of the web.

6. The apparatus of claim 1, wherein the mass measuring sensor arrangement and the caliper measuring sensor arrangement are configured to measure the web at locations at least partly common to the measurements.

7. The apparatus of claim 1, wherein the caliper measuring sensor arrangement comprises at least one optical sensor configured to provide information about a distance between the optical sensor and the opposite surface of the web with respect to the first surface, and at least one electromagnetic sensor element configured to provide information about the distance between the optical sensor and the stabilizing arrangement for determination of the caliper of the web.

8. The apparatus of claim 1, wherein stabilizing arrangement comprises an ejector configured to exert negative pressure on the web.

9. The apparatus of claim 1, wherein the stabilizing arrangement is configured suck the first surface of the web and the stabilizing arrangement in contact with each other for stabilizing vibration of the web in a direction crosswise with respect to the movement of the web.

10. A process system of producing a web, wherein the process system comprises the apparatus of claim 1 and at least one of the following: a paper machine, a pulp drier, a coating machine.

11. A controlling system, wherein the controlling system is configured to control the process system of producing a web of claim 9, the controlling system comprising a controller controlling at least one actuator of the process system on the basis of the measurements made by the caliper measuring sensor arrangement and the mass measuring sensor arrangement.

12. The controlling system of claim 11 comprising
one or more processors; and
one or more memories including computer program code;
the one or more memories and the computer program code configured to, with the one or more processors, cause the controlling system at least to:
measure caliper of the web and the at least one of the following: a basis weight, a water weight, a moisture content, a dry weight; and
control the at least one actuator of the process system on the basis of the measurements.

13. A method for measuring a moving web, the method comprising
stabilizing the moving web by a stabilizing arrangement by withdrawing gas from between the first surface of the web and a surface of the stabilizing arrangement, which includes at least a part of the mass measuring sensor arrangement;
measuring, by at least one microwave resonator sensor or at least one microwave transceiver sensor, weight of the web on the basis of at least one of the following from the moving web: a basis weight of the web and a dry weight; and a water weight of the web on the basis of at least one of the following: a water weight of the web and a moisture content of the web; and
measuring, by an optical caliper measuring sensor arrangement, caliper of the moving web.

* * * * *